(12) United States Patent
Peiffer et al.

(10) Patent No.: US 10,548,783 B2
(45) Date of Patent: Feb. 4, 2020

(54) FASTENING TAB WITH ADHESIVES HAVING DIFFERENTIAL TACKINESS

(71) Applicant: 3M INNOVATIVE PROPERTIES COMPANY, St. Paul, MN (US)

(72) Inventors: Andreas Peiffer, Neuss (DE); Siegfried R. Gabriel, Düsseldorf (DE)

(73) Assignee: 3M Innovative Properties Company, St. Paul, MN (US)

( * ) Notice: Subject to any disclaimer, the term of this patent is extended or adjusted under 35 U.S.C. 154(b) by 637 days.

(21) Appl. No.: 15/129,160

(22) PCT Filed: Mar. 27, 2015

(86) PCT No.: PCT/US2015/022908
§ 371 (c)(1),
(2) Date: Sep. 26, 2016

(87) PCT Pub. No.: WO2015/153327
PCT Pub. Date: Oct. 8, 2015

(65) Prior Publication Data
US 2017/0100288 A1    Apr. 13, 2017

(30) Foreign Application Priority Data
Mar. 31, 2014   (EP) .................................... 14162562

(51) Int. Cl.
*A61F 13/62* (2006.01)
*A61F 13/58* (2006.01)

(52) U.S. Cl.
CPC .......... *A61F 13/622* (2013.01); *A61F 13/581* (2013.01); *A61F 2013/583* (2013.01)

(58) Field of Classification Search
CPC .................. A61F 13/581; A61F 13/622; A61F 2013/582; A61F 2013/583
See application file for complete search history.

(56) References Cited

U.S. PATENT DOCUMENTS

| | | |
|---|---|---|
| RE24,906 E | 12/1960 | Ulrich |
| 3,932,328 A | 1/1976 | Korpman |
| (Continued) | | |

FOREIGN PATENT DOCUMENTS

| | | |
|---|---|---|
| EP | 1484041 | 12/2004 |
| WO | WO 2005-000180 | 1/2005 |
| (Continued) | | |

OTHER PUBLICATIONS

International Search Report for PCT International Application No. PCT/US2015/022908, dated Jun. 30, 2015, 3pgs.

*Primary Examiner* — Kathryn E Ditmer

(74) *Attorney, Agent, or Firm* — Colene H. Blank

(57) ABSTRACT

The present invention relates to improved fastening tabs, in particular to fastening tabs for disposable absorbent articles such as diapers or sanitary napkins. The fastening tab generally comprises a substrate and a first adhesive on the substrate. The substrate has at least one fastening region comprising one or more patches of a fastening material attached to the substrate. Each of the patches comprising a plurality of fastening elements, and exposed areas between the patches of fastening material that are free of fastening material. The first adhesive is adjacent to at least one fastening region. The first adhesive has a first tackiness and the exposed areas of the have a second tackiness. The second tackiness is lower than the first tackiness.

22 Claims, 3 Drawing Sheets

(56) References Cited

U.S. PATENT DOCUMENTS

| | | | |
|---|---|---|---|
| 4,710,536 A | 12/1987 | Klingen | |
| 4,973,326 A * | 11/1990 | Wood | A61F 13/622 24/450 |
| 5,019,071 A | 5/1991 | Bany | |
| 5,264,264 A * | 11/1993 | Shibata | A61F 13/58 428/41.8 |
| 5,389,438 A * | 2/1995 | Miller | A61F 13/58 428/355 RA |
| 5,851,205 A * | 12/1998 | Hisada | A61F 13/5512 604/390 |
| 2001/0056270 A1* | 12/2001 | Mizutani | A61F 13/551 604/385.02 |
| 2002/0095130 A1* | 7/2002 | Seitter | A61F 13/58 604/389 |
| 2007/0134489 A1* | 6/2007 | Neugebauer | A61F 13/15756 428/343 |
| 2011/0313389 A1* | 12/2011 | Wood | A44B 18/0065 604/391 |
| 2012/0204383 A1* | 8/2012 | Wood | A44B 18/0046 24/306 |
| 2015/0313775 A1* | 11/2015 | Kolic | A61F 13/625 604/389 |

FOREIGN PATENT DOCUMENTS

| | | |
|---|---|---|
| WO | WO 2012-112768 | 8/2012 |
| WO | WO 2012-158538 | 11/2012 |

\* cited by examiner

FASTENING TAB WITH ADHESIVES HAVING DIFFERENTIAL TACKINESS

CROSS REFERENCE TO RELATED APPLICATIONS

This application is a national stage filing under 35 U.S.C. 371 of PCT/US2015/022908, filed Mar. 27, 2015, which claims the benefit of EP Application No. 14162562.4, filed Mar. 31, 2014, the disclosure of which is incorporated by reference in its/their entirety herein.

The present invention relates to improved fastening tabs, in particular to fastening tabs for disposable absorbent articles such as diapers, incontinence briefs and sanitary napkins.

Fastening tabs are widely used in the hygiene industry. One important application of such fastening tabs relates to the closure system of diapers. These fastening tabs comprise a substrate having a manufacturer's end for attaching a tab to a disposable article, e.g., to the outer side of a diaper's ear and an opposite user's end which may be gripped by a user and attached to a landing zone of, e.g., the diaper. The user's end typically comprises a fastening material such as hook material for releasably adhering the fastening tab to, e.g., a corresponding loop material provided in the landing zone. Since it is generally undesirable that said fastening tab freely extends from, e.g., a diaper's ear, the user's end of the fastening tab is often folded around the diaper's ear and attached to the inner side of said diaper's ear. This technique is often referred to as the so-called "anti-flagging feature".

Two particularly advantageous fastening tabs are described in WO 2005/000180 A1 and WO 2012/112768 A1. These applications describe fastening tabs comprising regions of a hook material as well as adhesive regions, wherein the above-mentioned "anti-flagging feature" may be provided by the adhesive. However, the exposed regions of adhesive may adhere too strongly to the fibrous material of the inner side of the diaper's ear and thus cause delamination of fibers from the ear material once the fastening tab is detached from the inner side of the ear by a user. This is not only undesired due to aesthetic reasons, but the delaminated fibers may also cover part of the hook material on the fastening tab and thus compromise the fastening capabilities of the fastening tab.

It is therefore an object of the present invention to provide an improved fastening tab which overcomes the above-mentioned disadvantages. This object is achieved by a fastening tab according to claim 1 of the present invention. Preferred embodiments are described in the dependent claims.

Accordingly, the present invention relates to a fastening tab comprising a substrate having at least one fastening region. The at least one fastening region comprises one or more patches of a fastening material attached to the substrate, each of the patches comprising a plurality of fastening elements. The at least one fastening region further comprises one or more exposed areas within and/or in between the one or more patches of fastening material, the one or more exposed areas being free of fastening material. The fastening tab further comprises a first adhesive provided on the substrate adjacent to the at least one fastening region. The first adhesive has a first tackiness and the one or more exposed areas of the at least one fastening region have a second tackiness, said second tackiness being lower than the first tackiness.

The present invention is inter alia based on the idea to provide a first adhesive adjacent to the at least one fastening region in order to provide the "anti-flagging feature", whereas the one or more patches of the fastening material may be attached to the substrate by either a different adhesive or other means of attachment, such as ultrasonic, hot air bonding, which allow to adjust the tackiness in the one or more exposed areas of the at least one fastening region to be lower than the tackiness of the first adhesive. Thus, the second tackiness can be adjusted such as to make sure the fibers are not being delaminated from, e.g., a diaper's ear when detaching the user's end from such a diaper's ear.

According to a preferred embodiment of the present invention, the one or more patches of fastening material are attached to the substrate by a second adhesive. Preferably, the one or more exposed areas expose the second adhesive. Preferably, the second tackiness is the tackiness of the second adhesive after attachment of the one or more patches of fastening material to the substrate. In other words, the second adhesive may be a non-permanent adhesive having a short open time. It is preferably very sticky and has a good performance to bond the one or more patches of the fastening material to the substrate during manufacturing. However, once the one or more patches of fastening material have been attached to the substrate, the second adhesive is preferably dry and has a lower tackiness than the first tackiness.

Using two different adhesives advantageously allows for optimization of each of the adhesive material for their different functions. The material of the second adhesive may be chosen to optimize the bonding between the one or more patches of fastening material and the substrate during the manufacture of tabs or tapes including such tabs, while at the same time minimizing or even eliminating the risk of delamination of fibrous material from an absorbent article during the later use of the tab with the absorbent article. For example, the second adhesive may be a hot melt adhesive, in particular a hot melt adhesive having an set time and/or open time corresponding to the time typically desired and/or needed for the in-line production of tabs or tapes including tabs and being non-tacky or only slightly tacky thereafter. The first adhesive, on the other hand, may be for example a pressure sensitive adhesive having an endless open time or alternatively an open time typical of a shelf life of an absorbent article comprising a fastening tab. Moreover, at the same time, the first adhesive may be favourably optimized for facilitating anti-flagging properties in conjunction with an absorbent article without damaging the underlying material of the absorbent article.

Favourably, the first adhesive, has a tack value equal to or greater than 0.6 N/mm$^2$ in accordance with ASTM D 2979, where the probe has a diameter of 0.8 mm and the following conditions are used: separation rate 1 mm/min; dwell time 1 second; contact pressure 1950 kPa; and temperature and relative humidity (RH) 23° C. and 50%, respectively. More favourably the first tackiness has a tack value equal to or greater than 0.8 N/mm$^2$, and most favourably equal to or greater than 1.0 N/mm$^2$. Desirably the first adhesive has a tack value equal to or less than 3 N/mm$^2$. More desirably the first adhesive has a tack value equal to or less than 2.5 N/mm$^2$, even more favourably equal to or less than 2 N/mm$^2$, and most favourably equal to or less than 1.8 N/mm$^2$.

Favourably, the one or more exposed areas of the at least one fastening region of the tab has a tack value less than 0.6 N/mm$^2$ in accordance with ASTM D 2979, where the probe has a diameter of 0.8 mm and the following conditions are used: separation rate 1 mm/min; dwell time 1 second;

contact pressure 1950 kPa; and temperature and relative humidity 23° C. and 50%, respectively. More favourably the one or more exposed areas have a tack value equal to or less than 0.5 N/mm², and most favourably equal to or less than 0.4 N/mm². It will be appreciated that the one or more exposed areas may have a tack value down to 0 (zero) N/mm². For those preferred embodiments where the one or more exposed areas expose a second adhesive, it will be appreciated that said second adhesive will favourably have the desired tack values mentioned here in conjunction with said one or more exposed areas.

It will be appreciated that the aforementioned favourable tack values are those observed after the completion (e.g. after an open time of at least 24 hours) of a production of a fastening tab as described herein at ambient conditions (23° C. and 50% RH). Moreover, if for example a hot melt adhesive is used, it is the tackiness of the adhesive as present on the completed fastening tab after its setting and cooling down to ambient conditions which is of interest, rather than its high temperature tackiness during in-line production and bonding.

The second adhesive is preferably selected from a group of adhesives having (e.g. after an open time of at least 24 hours) a 90° peel adhesion to a smooth polyethylene test surface less than 2 N/inch, more preferably less than 1.5 N/inch, most preferably less than 1 N/inch as measured according to ASTM D3330, method F using a roll-down weight of 5,000 g and where the polyethylene test surface has an average surface roughness value $R_a$ of about 1.4 µm (e.g. measured using a laser profilometer and calculated in accordance with DIN 4768 and 4762).

Adhesives which are favorably useful as second adhesives include hot melt adhesives, in particular fast setting hot melt adhesives and/or hot melt adhesives which are not tacky or only slightly tacky at ambient temperatures (e.g. 23° C. and 50% RH). An example of such a hot melt adhesive is the adhesive LUNATACK™ HL 1696 X ZP marketed by H. B. Fuller. St Paul, Minn., USA. Other adhesives which may be favorably used as second adhesives include contact adhesives and latent-reactive adhesives (adhesives that are non-tacky at room temperatures but achieve a tacky state at higher temperatures, e.g. in excess of 50° C.). Latently reactive adhesive dispersions and films are for example marketed by Epurex GmbH, an associated company of Bayer MaterialScience AG, Leverkusen, Germany. Such films are composed on semi-crystalline polyurethane polymer of the type marketed under DISPERCOLL™ U into which surface-deactivated solid isocyanate particles are integrated, while such dispersions include a polyurethane dispersion of the aforementioned type in combination with deactivated solid isocyanate. The one or more patches of a fastening material may be attached to the substrate via a contact adhesive by providing contact adhesive on the underlying surface of the one or more patches as well as the appropriate area of the surface of the substrate to which the patch(es) are to be attached and then bringing the two surfaces together to allow for self-adhesion of the contact adhesive and thus bonding of the patch(es) to the substrate. The one or more patches of a fastening material may be attached to the substrate via a latent-reactive adhesive for example by positioning a latent reactive adhesive film between the one or more patches and the substrate and then raising the temperature to trigger melting and crosslinking of the polymer and thus bonding of the patch(es) to the substrate. Pressure sensitive adhesives may also be useful as second adhesives so long as the second tackiness is lower than the first tackiness. Coating weights of second adhesive may range from 5 to 100 g/m².

The first adhesive is preferably selected from a group of adhesives having (e.g. after an open time of at least 24 hours) a 90° peel adhesion to a smooth polyethylene test surface equal to or greater than 1 N/inch, more preferably equal to or greater than 1.5 N/inch, most preferably equal to or greater than 2 N/inch as measured according to ASTM D3330, method F using a roll-down weight of 5,000 g and where the polyethylene test surface has an average surface roughness value $R_a$ of about 1.4 µm (e.g. measured using a laser profilometer and calculated in accordance with DIN 4768 and 4762). To minimize any tendency towards fibrous material damage, favorably the first adhesive is selected from a group of adhesives having a 90° peel adhesion equal to or less than 10 N/inch, more desirably equal to or less than 9 N/inch, and most desirably equal to or less than 8 N/inch. Adhesives which are useful as first adhesives include pressure-sensitive adhesives which are selected from a group comprising (meth)acrylate and/or natural or synthetic rubber-based pressure-sensitive adhesives. Rubber-resin additives preferably comprise in addition to the rubber materials one or more tackifying resins in order to render the rubber materials tacky. Preferred examples of rubber-based pressure-sensitive adhesives are the polystyrene-polyisoprene block copolymers tackified with synthetic polyterpene resins. Suitable acrylate-based pressure-sensitive adhesives are disclosed, for example, in US Re 24,906 and U.S. Pat. No. 4,710,536. Suitable synthetic rubber based adhesives are described, for example, in U.S. Pat. Nos. 5,019,071 and 3,932,328. Coating weights of first adhesive may range from 5 to 100 g/m². Coating weights of first and second adhesives may be the same or different from one another.

Similar to that mentioned above in conjunction with favourable tack values, it will be appreciated that the aforementioned favourable peel adhesion values are those observed for a particular adhesive after the completion (e.g. after an open time of at least 24 hours) of a production of a fastening tab as described herein at ambient conditions (23° C. and 50% RH).

The tab preferably has a manufacturer's end e.g. for attaching the tab to a disposable article and a user's end opposite the manufacturer's end, wherein the at least one fastening region and the first adhesive is provided in the user's end. The first adhesive may be provided adjacent to the at least one fastening region towards or away from the manufacturer's end or on both sides of the at least one fastening region. It will be appreciated that for embodiments including two or more fastening regions, the first adhesive may be appropriately provided between, and thus adjacent to, two fastening regions. Desirably, the outermost end of the user's end is provided with a finger lift. And for such embodiments, if there is first adhesive provided adjacent to the fastening region away from the manufacturer's end, favourably it is provided between the fastening region and the finger lift.

Preferably, the first adhesive is provided directly adjacent to at least one of the one or more patches of the fastening material.

It is preferred that the one or more patches of fastening material comprise discrete patches such as discrete stripes of fastening material. Preferably, one or more exposed areas are discrete areas, such as discrete stripes.

It is also preferred that the one or more patches of fastening material are interconnected, wherein the one or more patches of fastening material preferably form a reticulated mechanical fastener comprising multiple strands of fastening material attached and/or integral to each other at bridging regions of fastening material. Examples of such a reticulated mechanical fastener are described in detail in WO 2012/112768 A1. Specific reference is made to this document and is incorporated by reference herein in its entirety, in particular in regard to the structure of such reticulated mechanical fasteners and the manufacturing thereof.

The present invention further relates to a tape comprising a plurality of fastening tabs as described above. The fastening tabs are arranged either individually or in endless form on the tab so that individual tabs can be cut from the fastening tabs. Preferably, the tab is provided in the form of a roll.

The present invention relates in addition to an absorbent article comprising at least one fastening tab as described herein. Such absorbent articles are typically disposable. Absorbent articles may comprise a top-sheet, a back-sheet and an absorbent core and the at least one fastening tab may be affixed to the top-sheet or back-sheet, in particular to the back-sheet. Absorbent articles may include diapers, incontinence briefs, and sanitary napkins.

Further preferred features are elucidated with reference to preferred embodiments which are shown in the following figures, which show:

Figure 1:
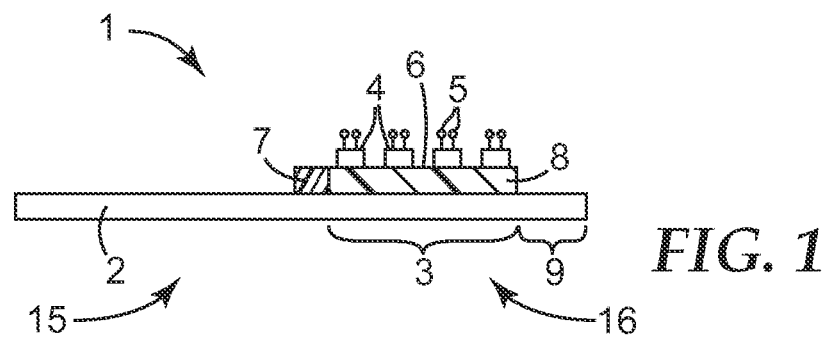
FIG. 1 is a schematic cross section of an exemplary embodiment of a fastening tab according to the present invention.
Figure 5:
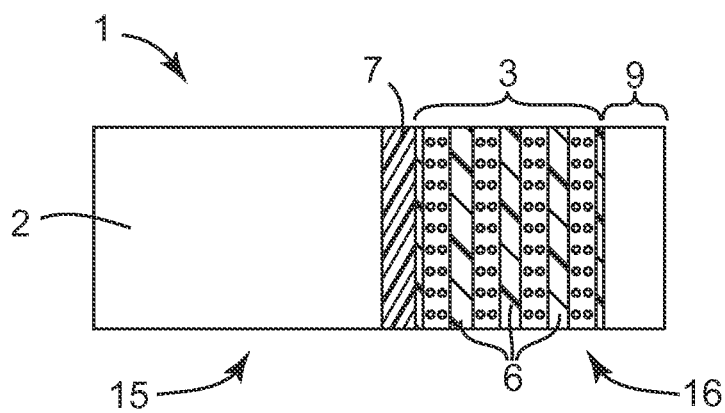
FIG. 5 is a schematic, top view of the fastening tab embodiment shown in FIG. 1.

FIG. 1 shows a schematic cross section of an exemplary embodiment of a fastening tab according to the present invention, while FIG. 5 shows a top view of the embodiment. The fastening tab 1 comprises a substrate 2 having a fastening region 3. The fastening region 3 comprises four patches 4 of a fastening material attached to the substrate 2 by means of a second adhesive 8. Each of the patches 4 comprises a plurality of fastening elements 5 (only two of which are shown for clarity purposes). The fastening region 3 further comprises three exposed areas 6 in between the four patches 4 of fastening material. These three exposed areas 6 are free of fastening material. The fastening tab 1 further comprises a first adhesive 7 provided on the substrate 2 adjacent to the fastening region 3. In the embodiment shown in FIGS. 1 and 5, the first adhesive 7 is provided directly adjacent to one of the four patches 4 of fastening material. The first adhesive 7 has a first tackiness. The exposed areas 6, in particular the second adhesive 8, has a second tackiness, wherein the second tackiness is lower than the first tackiness.

As can be appreciated from the fastening tab 1 shown in FIGS. 1 and 5, typically fastening tabs have a manufacturer's end 15 e.g. for attaching the fastening tab to a disposable absorbent article, such as a diaper, and an opposite user's end 16 e.g. for fastening and de-fastening the tab by the user. As can be appreciated in FIGS. 1 and 5, the fastening region 3 and the first adhesive 7 are located in the user's end. The outermost portion of the user's end being may be configured and arranged to include a finger lift 9 to facilitate handling of the user's end by the user in particular making it easier to grip the tab while fastening and de-fastening it. Desirably the finger lift 9 is free of fastening material and adhesive. It will be appreciated that a finger lift does not, however, necessarily need to be provided, and accordingly in such alternative embodiments, the illustrated fastening region may extend to the outermost end of the user's end.

Figure 2:
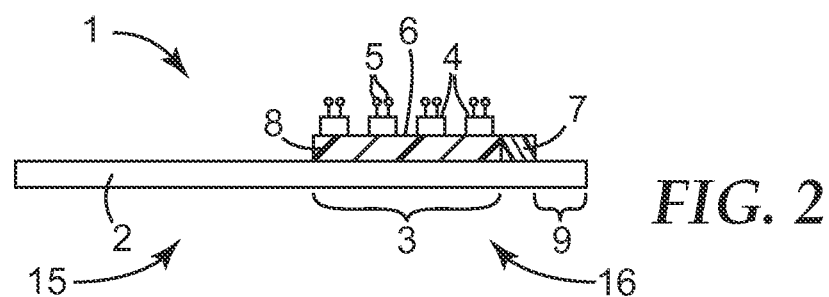
FIG. 2 is a schematic cross section of another exemplary embodiment of a fastening tab according to the present invention.
Figure 6:
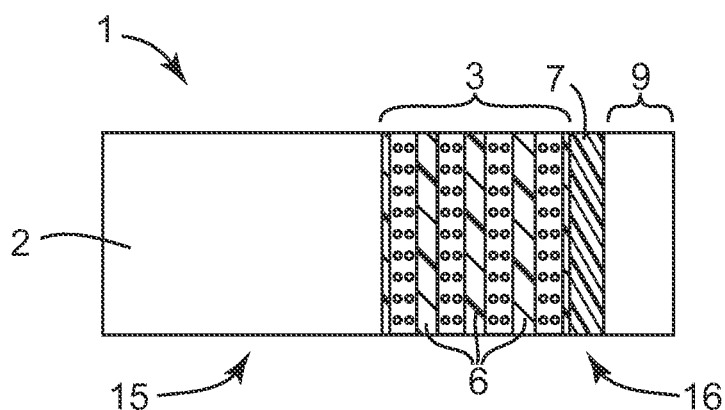
FIG. 6 is a schematic, top view of the fastening tab embodiment shown in FIG. 2.

In the embodiment shown in FIGS. 1 and 5, the first adhesive 7 is provided directly adjacent to the fastening region 3 on the side of the fastening region 3 towards the manufacturer's end of the tab. However, the first adhesive 7 may also be provided on the opposite side of the fastening region 3, i.e. the side that faces away from the manufacturer's end of the fastening tab. Such an exemplary embodiment is shown in FIGS. 2 and 6, where FIG. 2 provides a schematic cross-sectional view and FIG. 6 a top view. In FIGS. 2 and 6, it will be noted that the first adhesive 7 is positioned adjacent to the fastening region 3 distant to the manufacturer's end; in particular the first adhesive 7 is positioned between the fastening region 3 and the finger lift 9. In further preferred embodiments, the first adhesive may be favourably provided adjacent to both sides of the fastening region, i.e. adjacent to the side towards the manufacturer's end as well as to the side away from the manufacturer's end.

Figure 7:
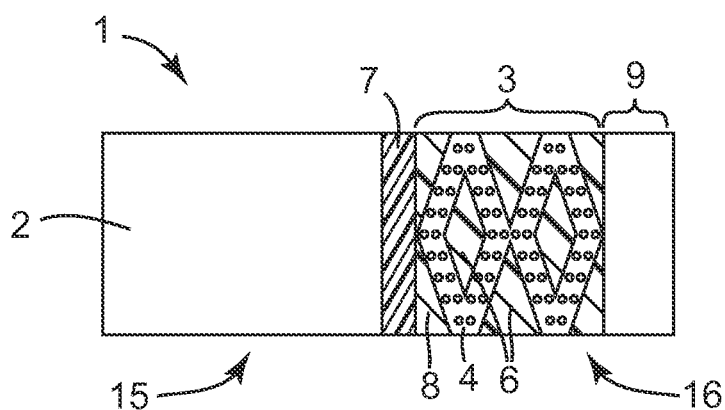
FIG. 7 is a schematic, top view of a further exemplary embodiment of a fastening tab according to the present invention.
Figure 8:
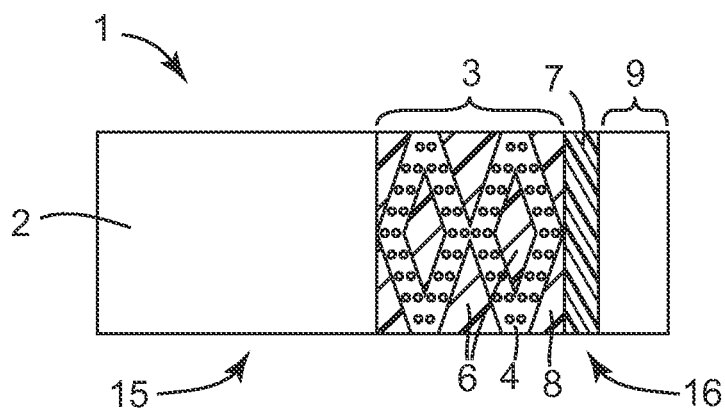
FIG. 8 is a schematic, top view of yet another exemplary embodiment of a fastening tab according to the present invention.

FIGS. 7 and 8 provide schematic top views of two more exemplary embodiments of fastening tabs according to the present invention. Similar to the previous illustrated embodiments, the fastening tabs 1 comprise a substrate 2 having a fastening region 3 with an first adhesive 7 provided adjacent to the fastening region and with the one or more patches 4 of fastening material being attached to the substrate 2 by means of a second adhesive 8. Here the one or more patches of fastening material is desirably provided in the form of a reticulated mechanical fastener comprising multiple strands of fastening materials attached and/or integral to each other at bridging regions of fastening material. In the illustrated embodiment, it can be seen that the strands are desirably integral to one another, so that the embodiment strictly speaking includes a single integral patch, wherein due to its open double-diamond form exposed areas 6 are provided therein. As shown in FIGS. 7 and 8, the first adhesive 7 may be provided adjacent to the fastening region 3 towards or away from the manufacturer's end, or alternatively first adhesive may be provided on both sides of the fastening region. In the embodiments shown in FIGS. 7 and 8, it will be seen that the first adhesive 7 is provided as a linear strip so that there may be exposed areas provided between the first adhesive 7 and the outward facing edge of the patch 4 towards the first adhesive. In alternative embodiments the first adhesive may be provided such that it follows the form of the outward facing edge of the patch towards the first adhesive or alternatively the patch may be provided with continuous linear outward facing edge, so that there are no exposed areas between the first adhesive and said edge of the patch.

From the exemplary embodiments provided herein and the discussion thereof, the person skilled in the art will readily understand that the patches of fastening material, the exposed areas and the first adhesive may be provided in different shapes. As mentioned above, patches of fastening material need not be discrete but may be interconnected. Strip-like patches may have varying cross sections or may be arranged in zig-zag patterns. In addition rather than providing stripes or interconnected or integral strands of fastening material, fastening tabs may also comprise a plurality of individual spots, which are preferably circular, of fastening material.

Figure 10:
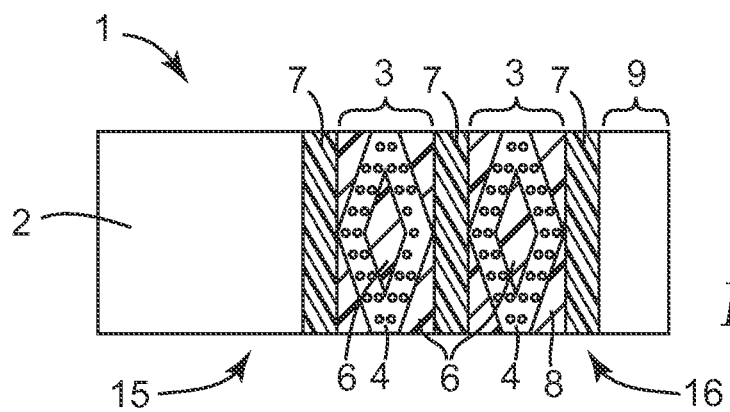
FIG. 10 is a schematic, top view of yet another exemplary embodiment of a fastening tab according to the present invention.

In other favourable embodiments, two or more fastening regions may be provided. For example, FIG. 10 provides a schematic top view of such an exemplary embodiment of a fastening tab 3. The fastening tab 1 comprises a substrate 2 with two fastening regions 3 with patches 4 of fastening material being attached to the substrate 2 by means of a second adhesive 8. In the illustrated embodiment, it can be seen that each fastening region has a single open diamond patch an exposed area 6 therein. First adhesive 7 is provided adjacent to each side of the fastening regions, so that the tab includes three linear strips of first adhesive as well as exposed areas between the strips and respective edges of the patches. Similar to that mentioned above, in alternative embodiments, the first adhesive may be provided such that it follows the form the edges of the patches which are facing towards the first adhesive or alternatively the edges of the patches which are facing towards the first adhesive may be configured as linear edges, so that there are no exposed areas between the first adhesive and said edges of the patches.

The substrate of fastening tabs described herein may be selected from a variety of films or sheetings including single-layered and multi-layered films, co-extended films, laterally laminated films or films comprising film layers. The layers of such films or sheetings may comprise various materials such as, for example, polypropylene, polyvinylchloride, polyethylene terephthalate, polyethylene, polyolefin copolymers or blends of polyolefins such as, for example, a blend of polypropylene, low density polyethylene and/or linear low density polyethylene, textiles, and non-woven and foamed materials. The thickness of the substrate is preferably between 30 microns and 500 microns, and more preferably between 40 and 150 microns. The base weight of the substrate is preferably between 15 and 500 g/m², more preferably between 20 and 300 g/m² and particularly preferably between 20 and 200 g/m².

Substantially any thermoplastic materials suitable for film production can be used to produce the one or more patches of fastening material. Preferred thermoplastic resins include polyesters, such as poly (ethylene terephthalate); polyamides, such as nylon; poly (styrene-acrylonitrile); poly (acrylonitrile-butadiene-styrene), polyolefins, such as polypropylene; and plasticized polyvinylchloride.

The plurality of fastening elements preferably have a hook shape and usually comprise a stem supported by the exposed major surface of a patch of fastening material and an enlarged section which is positioned at the end of the stem opposite to the exposed major surface. The fastening elements can also be formed by stem having no enlarged section at the end of the stem, wherein such stems are preferably essentially conical, cylindrical or pyramidal. Fastening elements suitable in the present invention can be manufactured from a wide range of materials including thermoplastic polymers such as, for example, nylon, polyester, polyolefins or any combination of these. The fastening elements preferably comprise the material of which the patch of fastening material is formed. The fastening elements may comprise male fastening elements, in particular male fastening elements selected from the group consisting of hook fasteners, mushroom-shaped fasteners, stem-shaped fasteners, cup-shaped fasteners, T-shaped fasteners and mixtures thereof. The height of the fastening elements may range from 0.1 to 0.4 mm.

Figure 3:
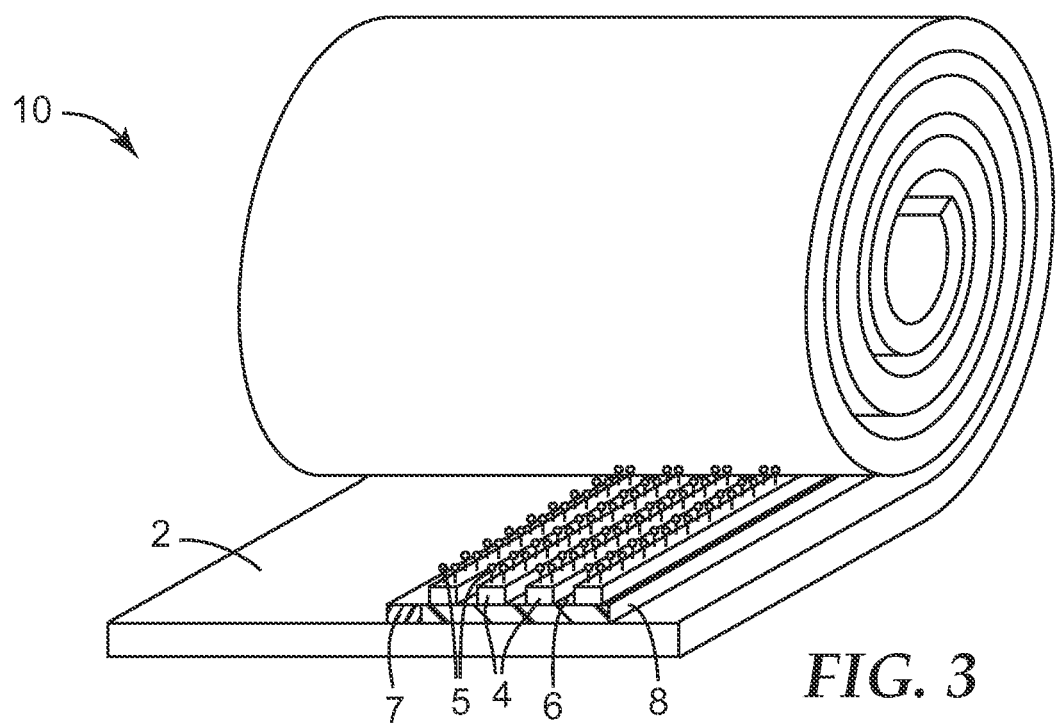
FIG. 3 is a schematic perspective view of an exemplary tape including fastening tabs of the type shown in FIG. 1 in an endless form.
Figure 9:
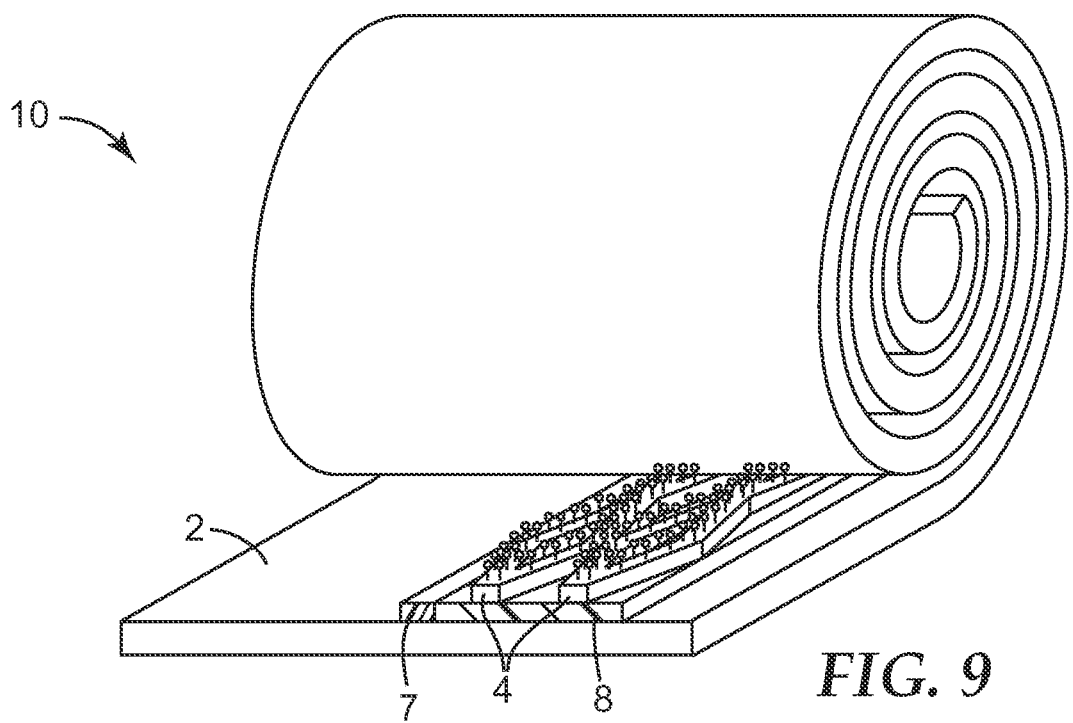
FIG. 9 is a schematic perspective view of another exemplary tape including fastening tabs of the type shown in FIG. 7 in an endless form.

The present invention further relates to a tape comprising a plurality of fastening tabs as described above. Exemplary embodiments of such tapes are shown in FIGS. 3 and 9, both favourably provided in the form of a roll. FIG. 3 provides a schematic perspective view of an fastening tape 10 including fastening tabs of the type shown in FIGS. 1 and 5, while FIG. 9 provides a schematic perspective view of an fastening tape 10 including fastening tabs of the type shown in FIG. 7. Desirably the fastening tabs are arranged in endless form on the tape 10 so that individual tabs can be cut from the fastening tape. Alternatively, the fastening tabs may be arranged individually on the tape for example spaced from each other along the machine direction.

Figure 4:
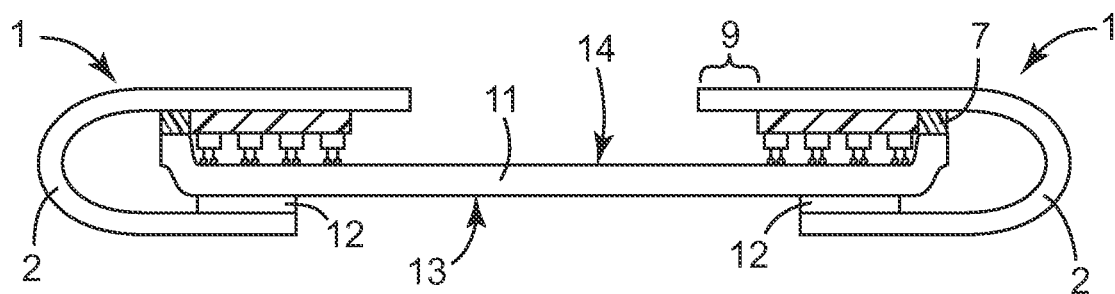
FIG. 4 is a schematic, partial cross section of an absorbent article, in particular a diaper, including two fastening tabs of the type shown in FIG. 1 attached to portions thereof, in particular to ears of the diaper.

FIG. 4 provides a schematic, partial cross section of an absorbent article including two fastening tabs of the type shown in FIG. 1 attached to portions of the article. In particular FIG. 4 provides cross section of a back portion of a diaper 11 across for example the two ear portions of the diaper. Although not shown in FIG. 4, absorbent articles in particular disposable absorbent articles, such as diapers and sanitary napkins, typically comprise a top sheet, a back sheet and an absorbent core. The top sheet is typically made of a nonwoven. As shown in FIG. 4, the fastening tabs 1 are affixed at their manufacturer's end to one side, normally the outer side, in particular to the back-sheet 13 of the diaper. The attachment can be achieved for example through a third adhesive 12 or any other suitable means. The fastening tabs 1 are typically folded over so that the user's end faces the opposite side, normally the inner side, in particular to the top-sheet 14 of the diaper 11 and the tabs are releasably attached to inner side, e.g. top sheet 14 via the first adhesive 7. In order to use the fastening tabs, a user may then detach the user's ends from the inner side (e.g. top sheet) for example by lifting the finger lifts 9, whereby the fastening elements 5 of the patches 4 of fastening material may then be fastened to a corresponding complementary engaging material (e.g. loop material) provided at the front portion of the diaper, e.g., on a landing zone. Since the tackiness of the exposed areas of the fastening regions of the tabs is lower than the tackiness of the first adhesive, an attachment of the exposed areas of the fastening regions to the inner side (e.g. the top sheet) of the diaper is minimized or avoided, which in turn minimizes or avoids damage to the inner side (e.g. the top sheet) of the diaper portion, as well as prevents blocking of the fastening material by delaminated material or fibers upon detachment of the user's ends from the inner side of the diaper for use. Furthermore damage to the inner side may be additionally minimized by favourably selecting the first adhesive to facilitate anti-flagging properties in conjunction with an absorbent article while at the same minimizing or avoiding damage to the underlying material of the absorbent article.

The invention claimed is:

1. A fastening tab comprising:
a substrate having at least one fastening region, the at least one fastening region comprising one or more patches of a fastening material attached to the substrate, each of the patches comprising a plurality of fastening elements, and one or more exposed areas therein and/or in between the one or more patches of fastening material, the one or more exposed areas being free of the fastening material; and
a first adhesive provided on the substrate adjacent to the at least one fastening region;
wherein the first adhesive has a first tackiness and the one or more exposed areas of the at least one fastening region have a second tackiness, said second tackiness being lower than the first tackiness, wherein the second tackiness has a tack value equal to 0 (zero) $N/mm^2$;
wherein the one or more patches of fastening material are attached to the substrate by a second adhesive and the one or more exposed areas expose the second adhesive and wherein the second tackiness is the tackiness of the second adhesive after attachment of the one or more patches of fastening material to the substrate, and wherein the tab has a manufacturer's end and an opposite user's end and wherein the at least one fastening region and the first adhesive are provided in the user's end.

2. The tab of claim 1, wherein the second adhesive comprises one or a combination of the following materials: a hot melt adhesive, a contact adhesive, a latent-reactive adhesive, and a pressure-sensitive adhesive.

3. The tab of claim 2, wherein the second adhesive is selected from a group of adhesives having a 90° peel adhesion to a smooth polyethylene test surface of less than 2 N/inch as measured according to ASTM D3330, method F using a roll-down weight of 5,000 g and where the polyethylene test surface has an average surface roughness value $R_a$ of about 1.4 μm.

4. The tab of claim 1, wherein the first tackiness has a tack value equal to or greater than 0.6 $N/mm^2$ as determined in accordance with ASTM D 2979, where probe has an diameter of 0.8 mm, and where the following conditions were used: separation rate 1 mm/min; dwell time 1 second; contact pressure 1950 kPa; and
temperature and relative humidity 23° C. and 50%, respectively.

5. The tab of claim 4, wherein the first tackiness has a tack value equal to or less than 3 $N/mm^2$.

6. The tab of claim 1, wherein the second tackiness has a tack value less than 0.6 $N/mm^2$ as determined in accordance with ASTM D 2979, where probe has an diameter of 0.8 mm, and where the following conditions were used: separation rate 1 mm/min; dwell time 1 second; contact pressure 1950 kPa; and temperature and relative humidity 23° C. and 50%, respectively.

7. The tab of claim 1, wherein the first adhesive is a pressure sensitive adhesive.

8. The tab of claim 1, wherein the first adhesive is selected from a group of adhesives having a 90° peel adhesion to a smooth polyethylene test surface equal to or greater than 1 N/inch as measured according to ASTM D3330, method F using a roll-down weight of 5,000 g and where the polyethylene test surface has an average surface roughness value $R_a$ of about 1.4 μm.

9. The tab of claim 8, wherein the first adhesive is selected from a group of adhesives having a 90° peel adhesion to the smooth polyethylene test surface equal to or less than 10 N/inch.

10. The tab of claim 1, wherein the first adhesive is provided adjacent to the at least one fastening region towards and/or away from the manufacturer's end.

11. The tab of claim 1, wherein the outermost end of the user's end is provided with a finger lift.

12. The tab of claim 11, wherein the first adhesive is provided between the at least one fastening region and the finger lift.

13. The tab of claim 1, wherein the first adhesive is provided directly adjacent to at least one of the one or more patches of fastening material.

14. The tab of claim 1, wherein the one or more exposed areas are discrete areas.

15. The tab of claim 1, wherein the one or more patches of fastening material comprise interconnected patches.

16. The tab of claim 1, wherein the one or more patches of fastening material comprise discrete patches.

17. The tab of claim 1, wherein the tab comprises two or more fastening regions.

18. A tape comprising a plurality of fastening tabs according to claim 1, wherein the fastening tabs are arranged either individually or in endless form on the tape in a cross section so that individual tabs can be cut from the fastening tape.

19. The tape according to claim 18, wherein the tape is provided in the form of a roll.

20. An absorbent article comprising at least one fastening tab according to claim 1.

21. The absorbent article according to claim 20, wherein the absorbent article further comprises a topsheet, a backsheet and an absorbent core and wherein the at least one fastening tab is affixed to the topsheet and/or the backsheet.

22. The absorbent article according to claim 20, wherein the absorbent article is a diaper, incontinence brief, or a sanitary napkin.

* * * * *